(12) United States Patent
Lenz

(10) Patent No.: US 8,740,985 B1
(45) Date of Patent: Jun. 3, 2014

(54) KNEE PROSTHESIS

(71) Applicant: Smith & Nephew, Inc., Memphis, TN (US)

(72) Inventor: Nathaniel Milton Lenz, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 13/691,728

(22) Filed: Nov. 30, 2012

(51) Int. Cl.
*A61F 2/38* (2006.01)

(52) U.S. Cl.
USPC .................. 623/20.32; 623/20.34; 623/20.21

(58) Field of Classification Search
CPC .................................. A61F 2/38; A61F 2/389
USPC ................. 623/20.21, 20.32–20.34
See application file for complete search history.

(56) References Cited

U.S. PATENT DOCUMENTS

| | | |
|---|---|---|
| 3,852,830 A | 12/1974 | Marmor |
| 3,878,566 A | 4/1975 | Bechtol |
| 4,193,140 A | 3/1980 | Treace |
| 4,731,084 A | 3/1988 | Dunn et al. |
| 4,770,659 A | 9/1988 | Kendall |
| 4,770,661 A | 9/1988 | Oh |
| 4,790,850 A | 12/1988 | Dunn et al. |
| 4,795,471 A | 1/1989 | Oh |
| 4,846,841 A | 7/1989 | Oh |
| 4,932,972 A | 6/1990 | Dunn et al. |
| 4,950,298 A | 8/1990 | Gustilo |
| 4,969,895 A | 11/1990 | McLoed et al. |
| 5,047,058 A | 9/1991 | Roberts et al. |
| 5,053,037 A | 10/1991 | Lackey |
| 5,100,408 A | 3/1992 | Lackey |
| 5,203,807 A | 4/1993 | Evans et al. |
| 5,282,803 A | 2/1994 | Lackey |
| 5,312,411 A | 5/1994 | Steele et al. |
| 5,358,529 A | 10/1994 | Davidson |
| 5,417,693 A | 5/1995 | Sowden et al. |
| 5,417,694 A | 5/1995 | Marik |
| 5,480,444 A | 1/1996 | Incavo et al. |
| 5,514,140 A | 5/1996 | Lackey |
| 5,549,688 A | 8/1996 | Ries et al. |
| 5,560,096 A | 10/1996 | Stephens |
| 5,569,261 A | 10/1996 | Marik et al. |
| 5,575,039 A | 11/1996 | Leifeld et al. |
| 5,575,793 A | 11/1996 | Carls et al. |
| 5,593,449 A | 1/1997 | Roberson |
| 5,597,379 A | 1/1997 | Haines et al. |
| 5,609,641 A | 3/1997 | Johnson et al. |
| 5,609,642 A | 3/1997 | Johnson et al. |
| 5,628,749 A | 5/1997 | Vendrely et al. |
| 5,667,511 A | 9/1997 | Vendrely et al. |
| 5,683,396 A | 11/1997 | Roberson et al. |
| 5,683,397 A | 11/1997 | Carls et al. |
| 5,683,398 A | 11/1997 | Carls et al. |
| 5,683,469 A | 11/1997 | Johnson et al. |

(Continued)

*Primary Examiner* — Jason-Dennis Stewart
(74) *Attorney, Agent, or Firm* — Ropes & Gray LLP

(57) ABSTRACT

Tibial inserts and tibial femoral systems are provided for improved knee reconstruction systems. External rotation of a knee joint implant is enhanced by modifications to the post, providing a recess that allows clearance of the post against the corners of a box wall within the femoral component. The rotation provides for a more natural knee joint motion of the implant. The depth, size, and location of the post relief may be modified for certain applications to provide both improved rotational motion and constraint against undesirable motion of the knee.

15 Claims, 13 Drawing Sheets

(56) References Cited

U.S. PATENT DOCUMENTS

| | | |
|---|---|---|
| 5,683,470 A | 11/1997 | Johnson et al. |
| 5,683,471 A | 11/1997 | Incavo et al. |
| 5,693,056 A | 12/1997 | Carls et al. |
| 5,702,459 A | 12/1997 | Hummer et al. |
| 5,702,460 A | 12/1997 | Carls et al. |
| 5,702,463 A | 12/1997 | Pothier et al. |
| 5,702,464 A | 12/1997 | Lackey et al. |
| 5,720,752 A | 2/1998 | Elliott et al. |
| 5,755,804 A | 5/1998 | Schmotzer et al. |
| 5,766,200 A | 6/1998 | Mazurek et al. |
| 5,810,829 A | 9/1998 | Elliott et al. |
| 5,824,105 A | 10/1998 | Ries et al. |
| 5,879,393 A | 3/1999 | Whiteside et al. |
| 5,954,770 A | 9/1999 | Schmotzer et al. |
| 6,123,728 A | 9/2000 | Brosnahan et al. |
| 6,165,221 A | 12/2000 | Schmotzer |
| 6,258,127 B1 | 7/2001 | Schmotzer |
| 6,325,828 B1 | 12/2001 | Dennis et al. |
| 6,364,911 B1 | 4/2002 | Schmotzer et al. |
| 6,428,577 B1 | 8/2002 | Evans et al. |
| 6,554,837 B1 | 4/2003 | Hauri et al. |
| 6,626,913 B1 | 9/2003 | McKinnon et al. |
| 6,645,251 B2 | 11/2003 | Salehi et al. |
| 6,660,039 B1 | 12/2003 | Evans et al. |
| 6,770,098 B1 | 8/2004 | Hauri et al. |
| 6,953,479 B2 | 10/2005 | Carson et al. |
| 6,969,393 B2 | 11/2005 | Pinczewski et al. |
| 6,974,481 B1 | 12/2005 | Carson |
| 6,986,791 B1 | 1/2006 | Metzger |
| 7,048,741 B2 | 5/2006 | Swanson |
| 7,101,401 B2 | 9/2006 | Brack |
| 7,306,609 B2 | 12/2007 | Schmotzer et al. |
| 7,326,252 B2 | 2/2008 | Otto et al. |
| 7,344,541 B2 | 3/2008 | Haines et al. |
| 7,371,240 B2 | 5/2008 | Pinczewski et al. |
| 7,572,292 B2 | 8/2009 | Crabtree et al. |
| 7,585,328 B2 | 9/2009 | Haas |
| 7,604,639 B2 | 10/2009 | Swanson |
| 7,662,156 B2 | 2/2010 | Carson |
| 7,682,362 B2 | 3/2010 | Dees |
| 7,794,467 B2 | 9/2010 | McGinley et al. |
| 7,992,771 B2 | 8/2011 | Yamamoto |
| 2008/0119940 A1 | 5/2008 | Otto et al. |
| 2010/0312351 A1 | 12/2010 | Belcher |
| 2011/0125279 A1 | 5/2011 | Lipman et al. |
| 2012/0197409 A1* | 8/2012 | McKinnon et al. ........ 623/20.27 |

* cited by examiner

KNEE PROSTHESIS

BACKGROUND

In total knee replacement (TKR) surgery, a surgeon typically affixes two prosthetic components to the patient's bone structure—a first to the patient's femur and a second to the patient's tibia. These components are typically known as the femoral component and the tibial component, respectively. The femoral component is placed on a patient's distal femur after appropriate resection of the femur. The femoral component is usually metallic, having a highly polished outer condylar articulating surface, which is commonly J-shaped when viewed from a medial or lateral side.

A common type of tibial component uses a tray or plateau that generally conforms to the patient's resected proximal tibia. The tibial component also usually includes a stem that extends into a surgically formed opening in the patient's intramedullary canal.

A plastic or polymeric (often ultra high molecular weight polyethylene) insert or bearing fits between the tray of the tibial component and the femoral component. This insert provides a surface against which the femoral component condylar portion articulates, i.e., moves in gross motion corresponding generally to the motion of the femur relative to the tibia. One type of design is a posterior-stabilized design in which the insert includes a post that fits within box walls and a posterior cam of the femoral component, with the posterior cam stabilizing the implant against anterior tibial sliding when the knee is flexed.

A common complaint of TKR patients is that the replaced knee does not function like a normal knee or does not "feel normal." The replaced knee does not achieve normal knee kinematics or motion and generally has a more limited range of motion than a normal knee. Currently available designs typically produce kinematics different than the normal knee during gait due to the complex nature of the knee joint and the motion of the femur and tibia relative to one another during flexion and extension. For example, it is known that, in addition to rotating about a generally horizontal axis during flexion and extension, the tibia also rotates about its longitudinal axis. Such longitudinal rotation is typically referred to as either external or internal rotation, depending on whether reference is being made to the femur or tibia, respectively.

Few currently available posterior-stabilized designs achieve this longitudinal rotation. Most currently available designs provide a limited space between the insert post and the box walls of the femoral component, to increase insert post strength and contact area between the femoral posterior cam and the insert post. The limited space between the insert post and the box walls would, in most cases, impede the ability of the post to rotate longitudinally—that is, either by external or internal rotation within the box wall, as would be the natural motion of a healthy knee. Because few designs achieve this longitudinal rotation, this impediment is not generally recognized.

FIG. 1A and FIG. 1B depict top views of a prior art knee system with a standard tibial post fitted inside a femoral box wall. The post 400 is seated within the box wall 200 to form the post/box-wall configuration 450. FIG. 1A depicts the configuration 450 with arrangement of the post 400 and the box wall 200 during extension, where the walls 402-408 of the post are situated in parallel with walls 202-208 of the box 200. As shown, the walls of the post 400 are disposed near but not in direct contact with the box walls from the femoral component 200. The separation is depicted by the distance "C." In many standard knee systems, the distance "C" is approximately 0.5-1.5 mm, allowing a small space around the perimeter of the post. When flexion occurs, axial tibial and femoral rotation is affected because a corner of the post contacts the sidewalls of the femoral box wall. FIG. 1B depicts the posterior lateral corner 420 butting against the box wall 206 and the anterior medial corner 422 butting against the box wall 204 in the prior art system during flexion as a result of tibiofemoral rotation in the direction of arrow "TFR."

Constructing a total knee prosthesis which replicates the kinematics of a natural knee has been an on-going challenge in the orthopedic field. Several attempts have been made and are well known in the prior art, including those shown in U.S. Pat. Nos. 6,264,697, 6,325,828, US2005/0143832, and US2008/0119940. Other systems have been designed to allow rotation by altering the surfaces of the box wall. However, modification of the box wall can reduce the effectiveness of the box in constraining both varus and valgus motion during flexion with tibial inserts that have a wider, constrained post. Other systems and approaches that attempt to more closely replicate the structure and function of the human knee produce modifications to the post that narrow its width. Those implementations, however, reduce the contact surface between the post and the posterior cam surface of the femoral component, which can lead to increased post deformation or wear in the cam and post contact region, and can reduce the amount of material in the post, thereby reducing its strength.

Existing designs leave room for improvement in simulating the structure and operation of actual knee joints.

SUMMARY

Disclosed herein are devices that help facilitate a more natural motion in the tibial and femoral components of a reconstructed, replaced knee. In general, the tibial components include a tibial insert post that fits within a box wall of the femoral component and rotates therein. The post has anterior, posterior, medial and lateral walls, with a recess disposed on either the medial or lateral side of the post. The recess creates clearance with the femoral posterior-stabilized box wall during flexion and extension. This clearance allows relative femoral and tibial rotation to occur (longitudinal rotation), to track a more natural motion in the knee during flexion and extension. The width of the post is maintained across the posterior portion, thus helping maintain the strength of the post.

In certain implementations, the tibial insert has a base, a post with a vertical axis, a medial and a lateral sidewall, a posterior and an anterior face, a superior end, and an inferior end that extends from the base. The insert includes a first junction between the anterior face and medial sidewall, a second junction between the anterior face and the lateral sidewall, and a recess in the medial sidewall that extends across the first junction. In certain applications, the recess has a first boundary disposed along the medial sidewall substantially parallel to the vertical axis and a second boundary disposed along the medial sidewall substantially perpendicular to the vertical axis. The second boundary can extend across the first junction and, in some cases, protrude along the inferior region of the anterior face.

The posterior face of the insert is preferably configured with a first width between medial and lateral sidewalls along the posterior face, while the anterior face has a second width between the second boundary and lateral sidewall, that first width typically being greater than the second width, to help maintain strength in the post. In certain implementations, a shelf is disposed along the medial sidewall, extending substantially perpendicular to the first boundary and may be disposed superior to the base. The recess has a depth, as measured from the medial sidewall, and that depth may be variable. Certain implementations provide the recess at a first depth measured from the first boundary, wherein the first depth has a value of about 0.25 mm to about 1.5 mm. The first depth may also fall within that range, for example about 0.5 mm. In many applications, the recess depth will vary, including a minimum depth and a maximum depth. The minimum depth may be found in the inferior region of the recess, such that the recess slopes from smaller depth at the inferior or shelf end of the post to a deeper depth at or near the superior end.

Orthopedic surgical systems are also contemplated that incorporate improved tibial posts. In certain embodiments, a knee prosthesis system is disclosed, having a femoral component having first and second condylar surfaces, a tibial tray, and a tibial insert according to any of the embodiments described herein. The tibial insert is configured with first and second bearing surfaces that mate with the respective first and second condylar surfaces, providing an interface about which the condylar surfaces can articulate.

The femoral component includes a box receptacle that receives the post. In certain embodiments, the receptacle has a first set of opposing walls and a second set of opposing walls, a first wall of the first set of opposing walls being near the medial sidewall at a position inferior to the first boundary and being spaced away from the medial sidewall at a position superior to the first boundary. In certain preferred applications, one of the sets of opposing walls are positioned on the anterior and posterior sides of the box and provide respective cam surfaces that abut the posterior and anterior sides of the post during flexion/extension.

The post, with its recess, can rotate axially about the vertical axis of the post, allowing the tibial component to rotate longitudinally. That motion can, in some implementations, move a portion of the anterior face into alignment with the first (medial) wall of the box. In operation, rotating the post axially about the vertical axis moves a portion of the medial sidewall away from the first wall. In various system implementations, rotating the post axially about the vertical axis moves the recess toward the medial sidewall.

Methods of actuating a knee prosthesis are also contemplated. A base is provided, with a post extending from the base, along with a femoral component having a slot disposed generally between two condylar surfaces. Actuating the prosthesis can involve contacting a first wall of the slot with a first portion but not a second portion of a medial surface of the post, contacting a second wall of the slot with a lateral surface of the post; and rotating the post angularly within the slot to align the second portion toward the first wall. In certain implementations, aligning the second portion toward the first wall reduces contact between the second wall of the slot and the lateral surface of the post. The second portion of the medial surface can extend from the medial surface to an anterior surface of the post. In certain applications, rotating the post moves the anterior face into contact with the first wall. When rotating the post, an anterior wall of the slot lifts upwardly with respect to the slot. In certain methods, the post is actuated by a cam surface disposed within the slot.

Methods of treatment are also included. Representative methods involve installing an orthopedic insert within a joint and installing an articulating housing about or within which the insert can rotate axially. The insert has a means for facilitating the rotation of at least a portion of the insert (such as a tibial post) within a portion of the housing (such as a femoral component). In certain implementations, the insert has a recess or other clearance surface that allows it to clear a boundary of the housing during rotation. In certain implementations, the rotation occurs through an angle of motion that approximates relative rotation between the insert and the housing, as would occur in a normal joint, such as a knee.

BRIEF DESCRIPTION OF THE FIGURES

The foregoing and other objects and advantages will be apparent upon consideration of the following detailed description, taken in conjunction with the accompanying drawings, in which like reference characters refer to like parts throughout, and in which.

DETAILED DESCRIPTION

Disclosed herein are devices and systems used for orthopedic surgeries that provide a more natural motion between the tibial and femoral components of a reconstructed knee. Devices disclosed herein include tibial inserts that are used with femoral components to provide a more natural knee motion for a patient who has undergone total knee replacement. The tibial post has a sidewall with a recess that allows for better tibial and femoral rotation during flexion and extension of the knee. In general, a tibial insert post is provided with anterior, posterior, medial and lateral walls, and with a recess disposed on either the medial or lateral side of the post. The recess creates clearance with the posterior stabilized box wall of the femoral component during flexion and extension. This clearance allows femoral/tibial rotation to occur, to provide a more natural motion in the knee during flexion and extension. The width of the post is maintained across the posterior portion to minimize the reduction of the strength of the post.

While a width reduction or relief cutout of a tibial post decreases rotational interference, it may also reduce the constraint provided by the post for other types of motion. For example, the reduced post may provide less constraint on varus and/or valgus motion of the knee compared to a full standard posterior-stabilizing post. Thus, the design and shape of a post relief can be chosen to manage this tradeoff between allowing natural tibiofemoral rotation and providing adequate constraining on other types of motion. The relief design can leverage the native anatomy of a patient's knee to increase performance of an implant and provide both natural motion and sufficient support to the knee. For example, if the bone and surrounding soft tissue of a patient's knee is strong enough to resist valgus motion but not varus motion, a post can be provided with a medial relief. Such a post allows for natural rotation and resists varus motion that the knee may not be strong enough to resist on its own. The post may have reduced constraint against valgus motion, but such motion is resisted by the patient's native anatomy, and thus the implant leverages the patient's anatomy to achieve both natural motion and adequate constraint against harmful varus and valgus motions. Likewise, if a patient's native anatomy is strong enough to resist varus motion but not valgus motion, a post can be provided with a lateral relief, rather than a medial relief. The lateral relief can provide constraint on valgus motion and a reduced constraint on varus motion, which is supplemented by the strength of the patient's anatomy to provide sufficient support against harmful motion while also providing adequate natural motion during flexion and extension.

Figure 1A:
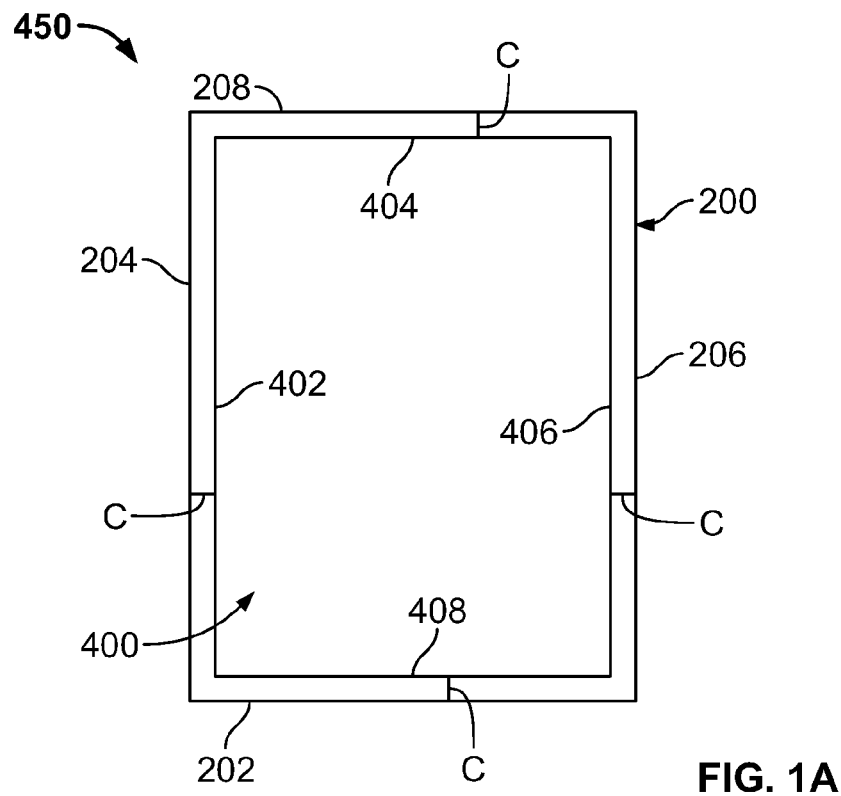
FIG. 1A depicts a top view of a prior art tibial post joined with a femoral box wall during knee extension.
Figure 1B:
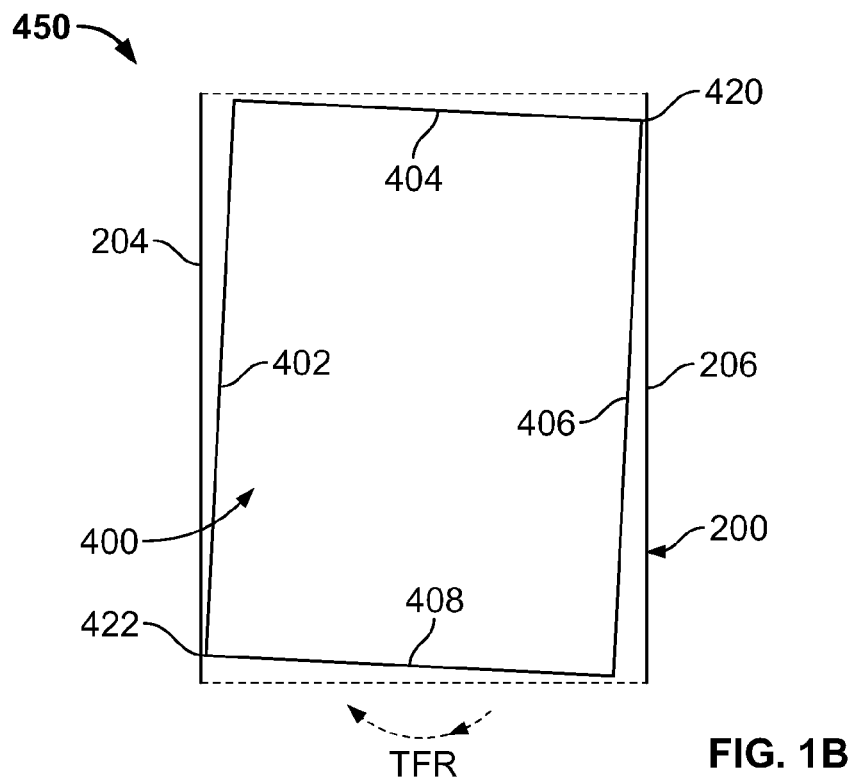
FIG. 1B depicts the tibial insert and femoral box wall of FIG. 1A during knee flexion.
Figure 2A:
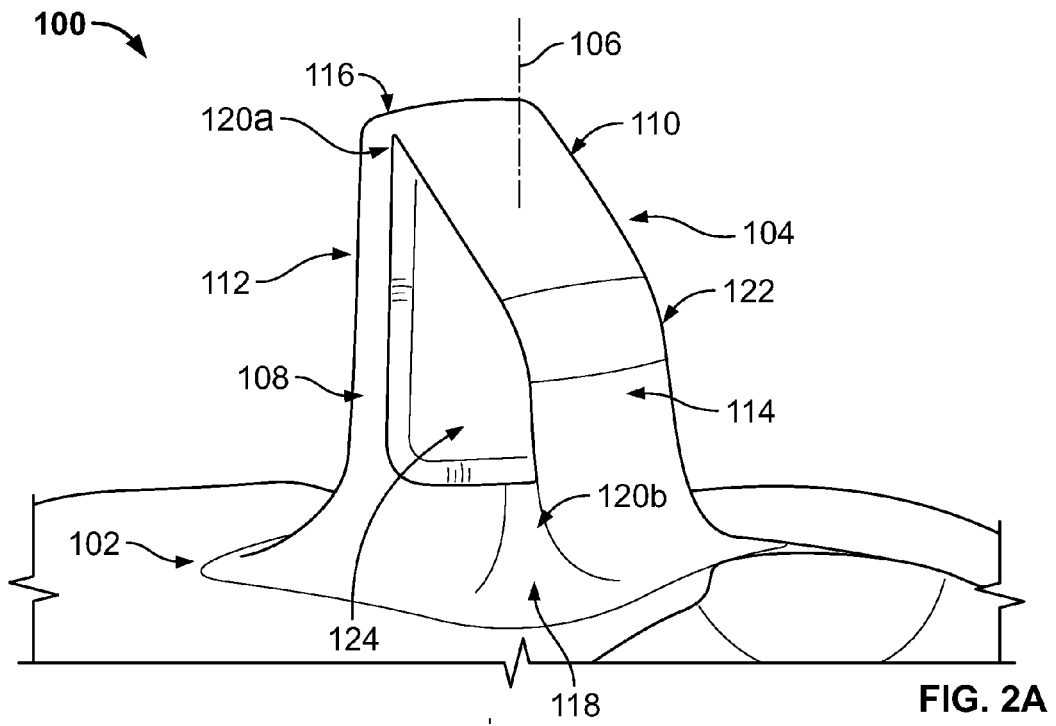
FIGS. 2A-2C depict perspective views of a tibial insert used in a total knee replacement system.

FIG. 2A depicts a medial/anterior view of a tibial insert 100 for use in a total knee replacement system. The insert 100 includes a tibial base section 102 which receives condylar surfaces from a femoral component. The insert 100 also includes a post 104 that extends from the base 102, into a femoral box wall of the femoral component, as described below. The post 104 has a vertical axis 106 that extends longitudinally through the post. The post 104 also includes a medial sidewall 108 and a lateral sidewall 110, a posterior face 112 and an anterior face 114. The superior portion 116 is disposed at the top of the post and an inferior portion 118 is disposed at the interface between the post and the base 102. In certain embodiments, the post and base are coextensive or co-molded, and the interface 118 is a continuous juncture between the two components.

Figure 2B:
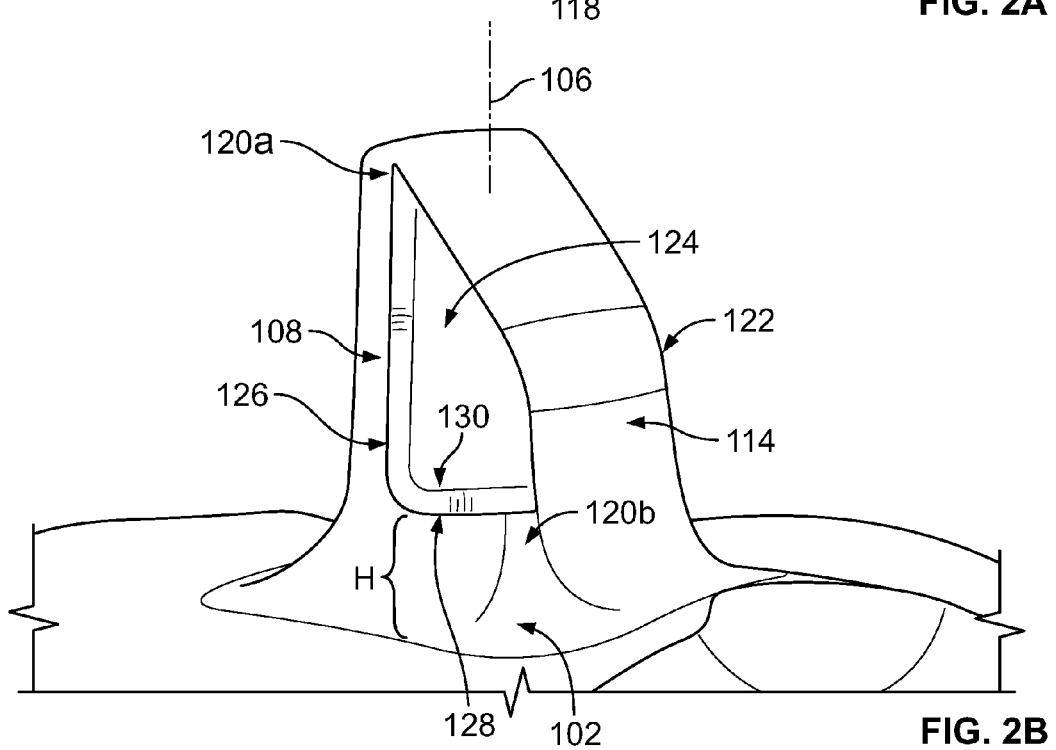

As shown in FIGS. 2A and 2B, the post 100 includes a first junction 120 between the anterior face 114 and the medial sidewall 108. A second junction 122 is disposed between the lateral sidewall 110 and the anterior face 114. As shown, a recess 124 is also included on the medial sidewall 108. The recess 124 extends from the medial sidewall, across the junction 120 and along an initial portion of the anterior face. The junction 120 is bifurcated, having an upper portion 120a disposed posterior and above the recess 124 and a lower portion 120b disposed anterior and below the recess 124. As shown, the recess 124 includes a first boundary 126 that extends substantially parallel to the vertical axis 106 and a second boundary 128 that extends substantially perpendicular to the vertical axis 106. The first boundary 126, as shown, provides a vertical wall within the medial wall of the post. The lower boundary 128 creates a shelf 130 that extends from the boundary into the medial wall 108. As shown, the shelf 128 is disposed above the base 102 by a height "H."

Figure 2C:
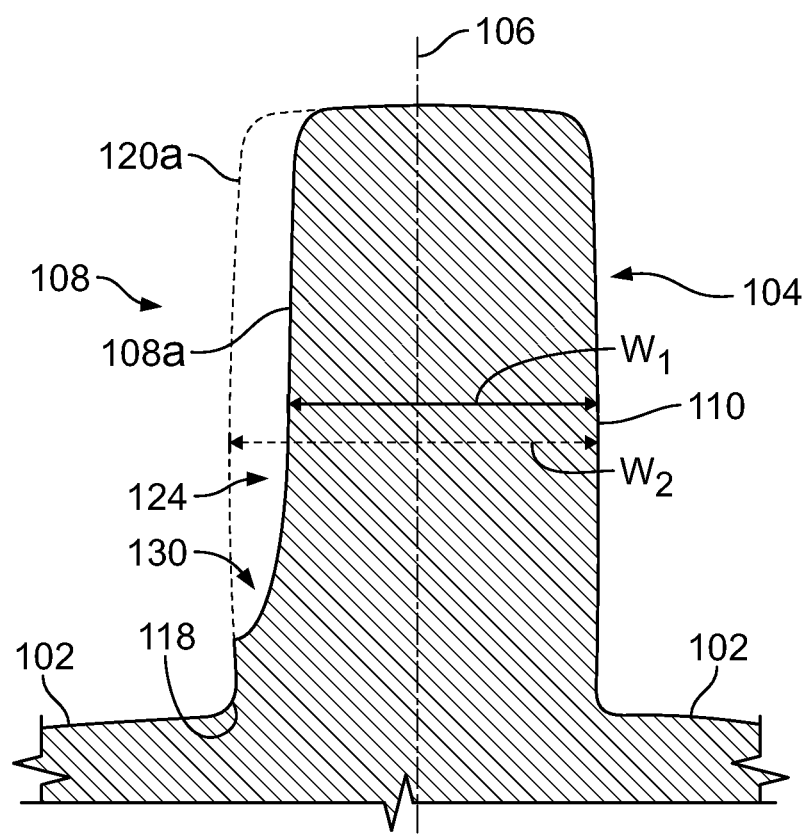

FIG. 2C depicts the post 104 from an anterior cross-sectional view. As shown, the recess 124 produces an anterior portion of the post that is narrower than the posterior portion. The anterior portion has a width W1 that extends from the lateral sidewall 110 to an inner surface 108A of the medial sidewall. The posterior portion of the post 104 has a wider width W2 that extends from the lateral sidewall 110 to the edge of the junction 120A on the medial side of the post.

FIG. 2C illustrates the depth of the recess area 124 extending into the medial wall. The depth can be variable or generally constant. The depth is preferably within the range of about 0.25 mm to about 3 mm and covers approximately the anterior 60% to 70% of the medial side of the post. As shown, the recessed area reduces the post width on the anterior side, decreasing it towards the superior edge of the post in a linear or curved manner. Depending on the overall width of the post, the width reduction in the area of the recess 124 may be within the range of about 3% to about 20% of the overall post width. This recess (and the shelf 130) is positioned at a height "H" from the base of the post, as shown in FIG. 2B. The height "H" in FIG. 2B can vary, for example, from about 1 mm to about 20 mm.

FIGS. 3A-3D depict an orthopedic implant system 300 having an insert 100 with a femoral component 200. The insert 100 is coupled with a tibial component 150. The femoral component 200 has a medial condylar section 214 and a lateral condylar section 216 with a trochlear grove 209 joining the lateral and medial condylar sections. The medial and lateral condylar sections 214 and 216 are disposed apart from each other to form an intracondylar recess or notch. Each condylar section 214 and 216 has a distal region 228 and 226, respectively, for engaging a portion of a tibial component or the insert 100 when the knee joint is extended and partially flexed and a posterior portion 222 and 224, respectively, for engaging a portion of the tibial component or insert 100 when the knee joint is flexed at angles of substantially 90 degrees or greater. In use, the insert 100 fits with the femoral component 200 by inserting the post 110 into the slot 202 formed within the femoral component 200. The slot 202 is surrounded by four walls (a "box wall") comprising medial side wall 204, lateral side wall 206, posterior cam surface 210 and anterior cam surface 208.

Figure 3A:
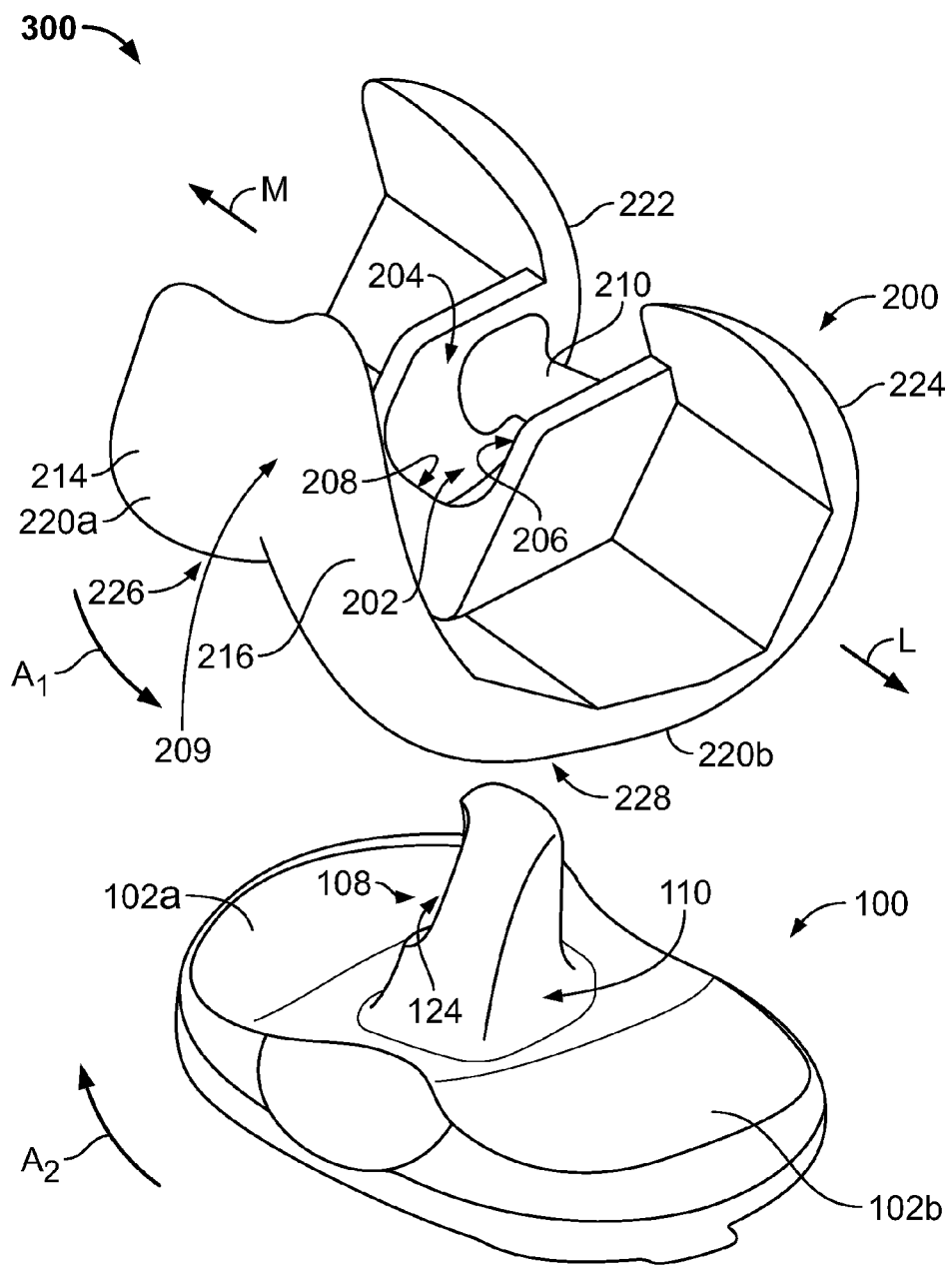
FIG. 3A-3D depict a total knee replacement system having a femoral component and a tibial insert.
Figure 3B:
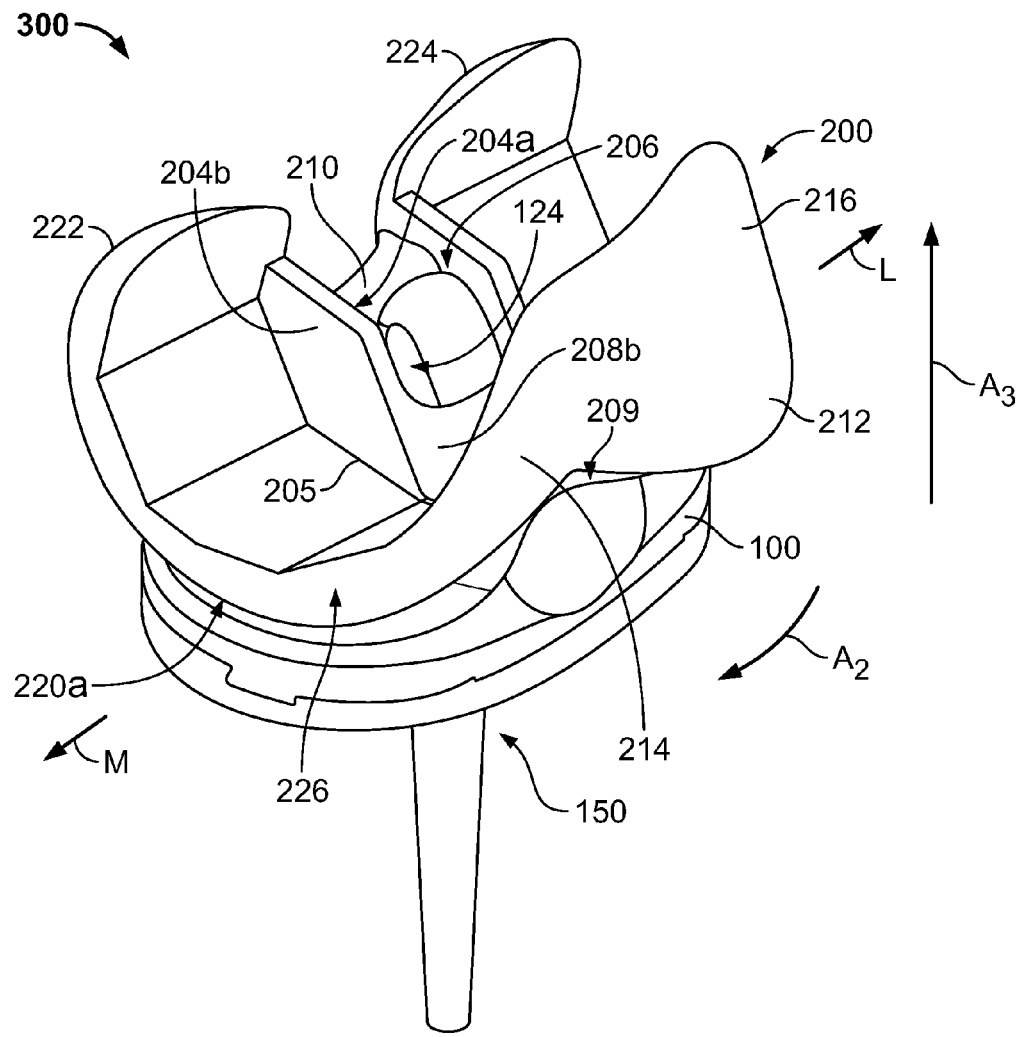

As shown in FIG. 3B, the recess 124 is located on the medial anterior portion of the post 110 and disposed along the inside portion 204a of medial wall 204. The medial wall 204 includes an outer face 204b and a lower border 205. During flexion and extension, the femoral component 200 articulates with respect to the insert 100 as the surfaces 220a and 220b articulate with respect to the medial portion 102a and the lateral portion 102b of the base, respectively.

Figure 3C:
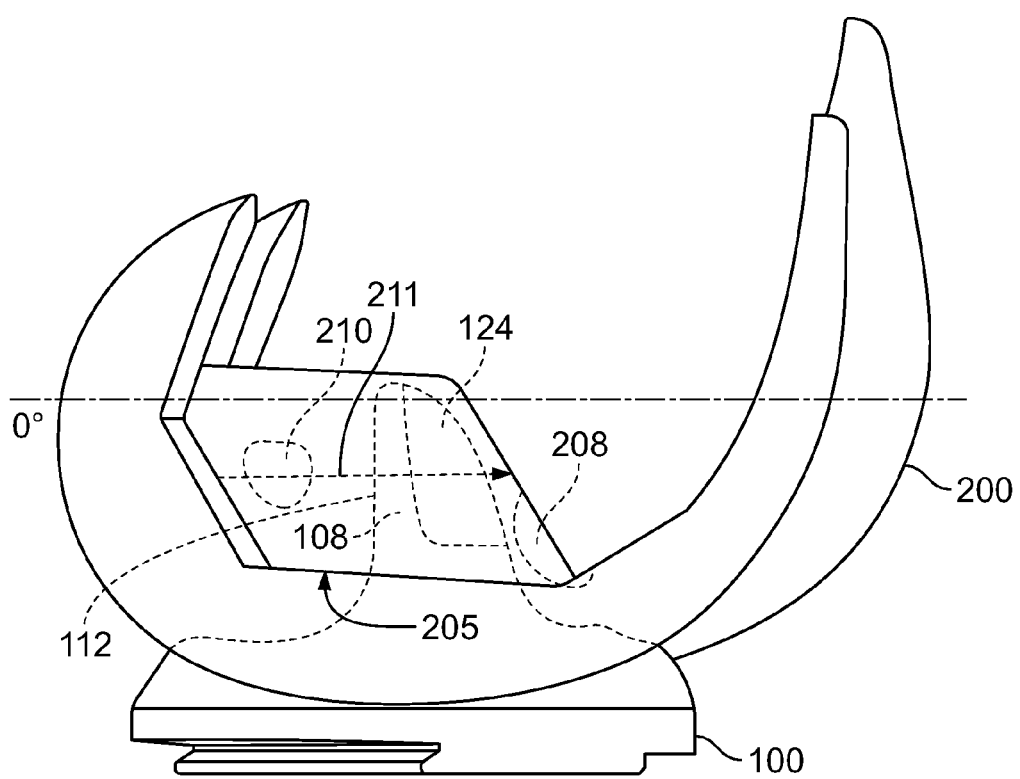
Figure 3D:
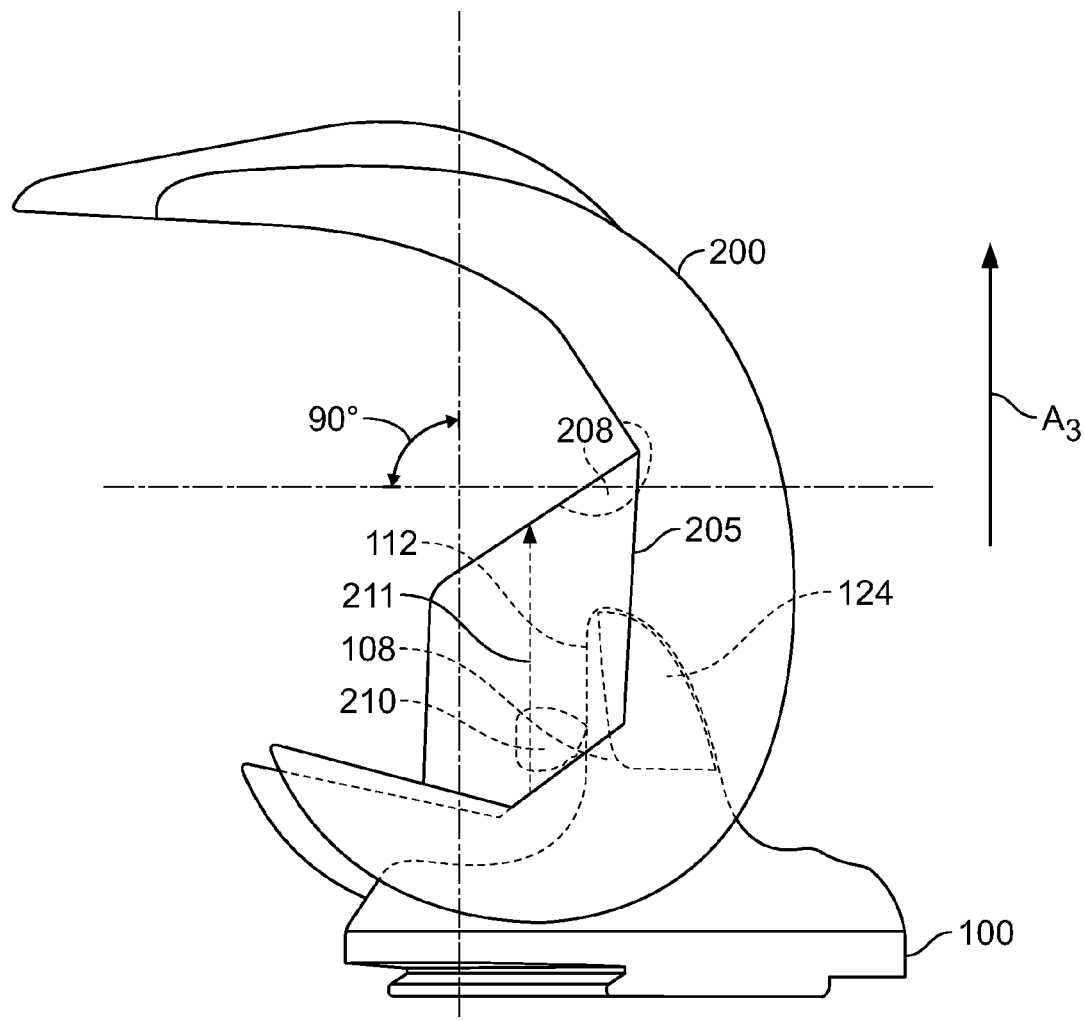

FIGS. 3B and 3C depict the system 300 during full knee extension. As the knee flexes and the femoral component and the insert articulate with respect to each other, they rotate axially relative to each other about the longitudinal axis 106 of the post 110. In particular, the femoral component rotates along arrow A1 and the insert articulates axially along the arrow A2. As articulation and relative rotation occur, the femoral component and the insert 100 will separate along the anterior side, with the anterior portion of the femoral component rising along the direction of arrow A3. As that occurs, as shown in FIG. 3D, the interface 124 rotates axially along the path of arrow A2, and the lower border 205 of the box wall rises vertically along the arrow A3. During that process, the recess 124 allows the anterior portion of the post 110 to clear the corner of the medial wall 204.

Figure 4A:
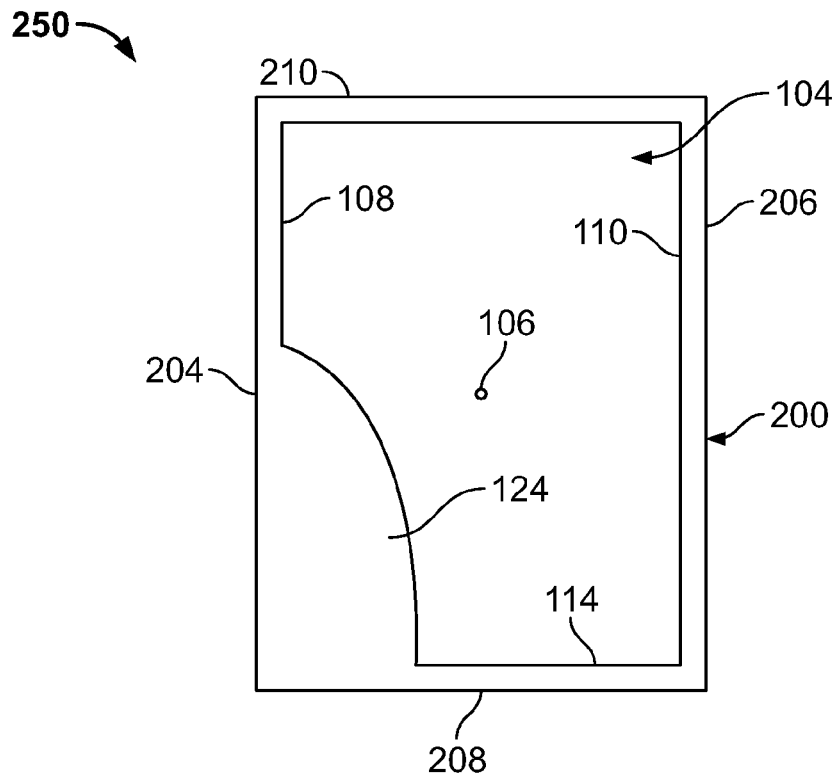
FIG. 4A depicts a top view of an improved tibial insert combined with a femoral box wall during extension of the knee.
Figure 4B:
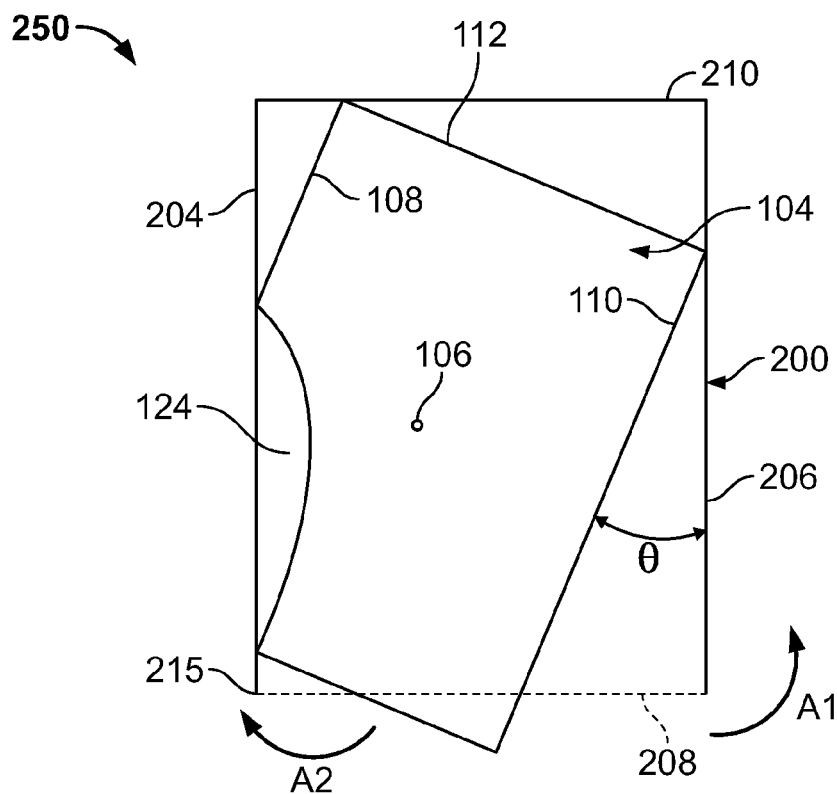
FIG. 4B depicts a tibial post combined with a femoral box wall during flexion of the knee.

The top view perspectives of FIGS. 4A and 4B illustrate the relative rotation between the tibial insert/post and the femoral component, providing a more free and natural knee rotation. FIG. 4A depicts the post 104 fitted within the box wall 200 of the femoral component, forming the combined structure 250 during knee extension (see FIGS. 3A-3D). Arrows A1 and A2 in FIG. 4B depict the relative rotation of the insert post 104 and the box walls 200, respectively, during flexion. During flexion, because of the recessed area 124, the anterior medial portion of the post 104 can clear the anterior medial corner 215 of the box walls 200, allowing the post 104 to rotate about the vertical axis 106 to the angle θ, thereby providing rotation that more closely matches the relative tibial/femoral rotation of a normal knee. The flexion of the knee also causes the cam surface 208 to rise past the superior end of the post, as shown in FIG. 3D, allowing the anteriolateral corner of the post to clear the cam, as shown in FIG. 4B. In certain implementations, the angle θ is approximately 5 to 15 degrees. In certain preferred embodiments, the angle θ is about 5-10 degrees. In some implementations, the post can rotate sufficiently far that the recess 124 faces or aligns with the medial wall 204a of the box 200.

Providing the post with a recess on the medial wall thus allows the post and box walls to rotate, with respect to each other, for more natural knee movement compared to prior art systems. Because the posterior surface 112 is maintained at its full width $W_2$, the post 104 can also maintain contact with the posterior surface 210 of the box wall 200, during flexion, to help maximize the strength of the implant. In this way, the improved insert post achieves a balance of more natural rotation during flexion but with strength and stability during extension.

Figure 5A:
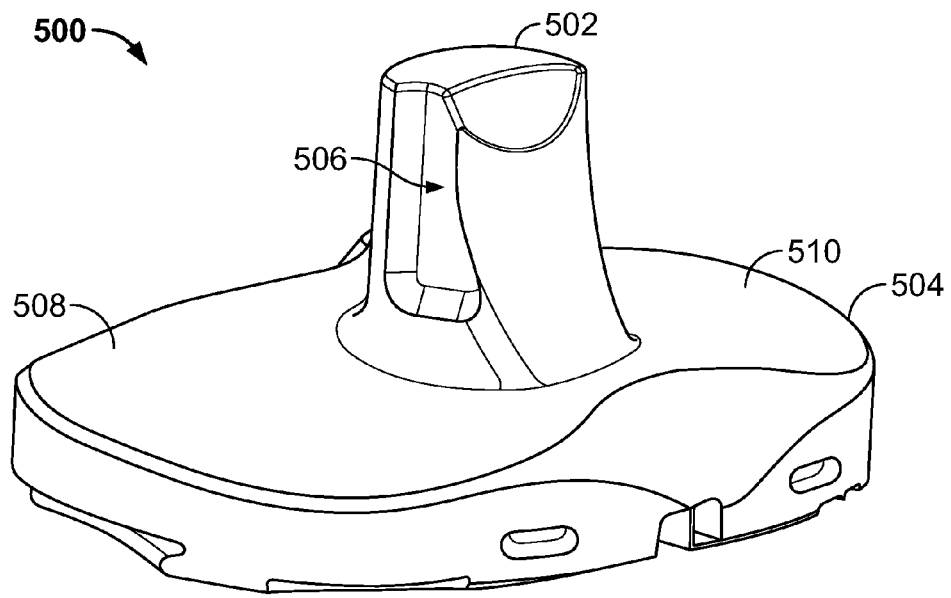
FIG. 5A depicts a tibial insert having a medial post relief.
Figure 5B:
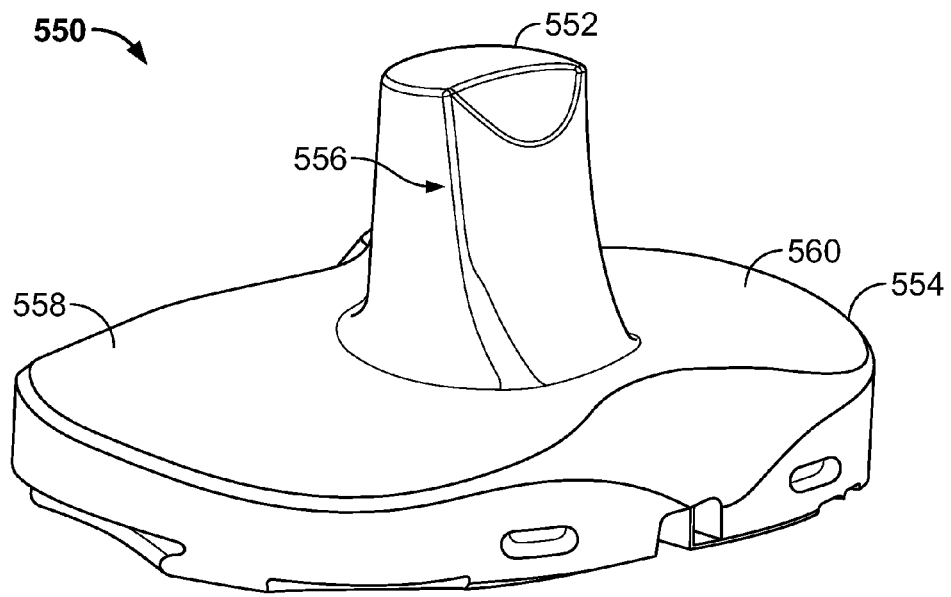
FIG. 5B depicts a tibial insert having a standard constrained post.
Figure 6:
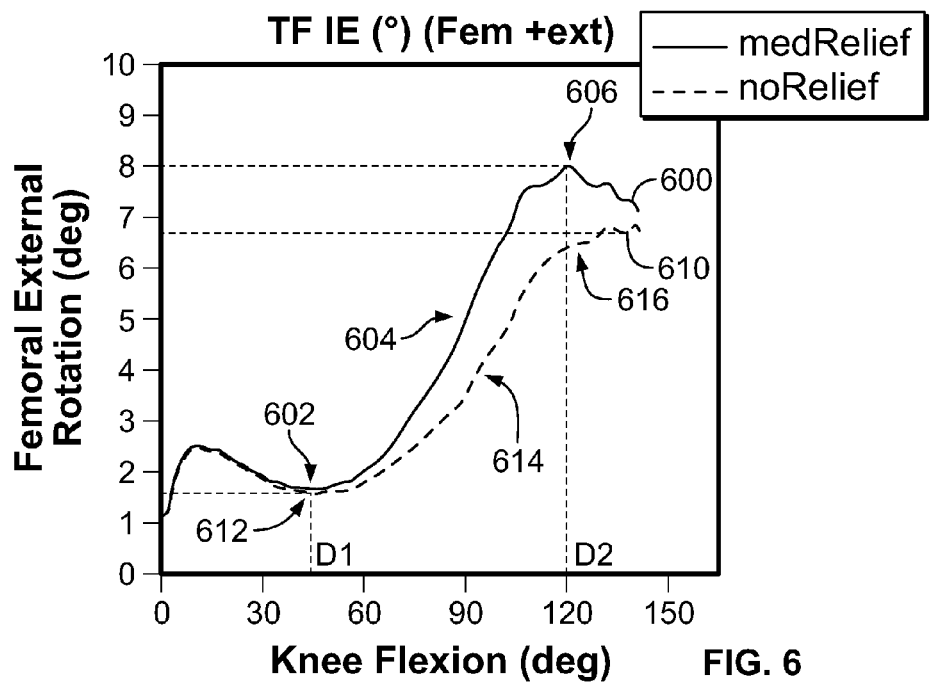
FIG. 6 depicts rotational test data for the inserts shown in FIGS. 5A and 5B.

The beneficial effect of allowing for external rotation of the femoral implant component relative to the tibial implant component, such as those illustrated in FIGS. 3A-4B, can be demonstrated by comparing rotation of an implant that employs a tibial insert having a medial relief with rotation of an implant that employs a tibial insert having a standard posterior-stabilizing post. FIGS. 5A-6 illustrate the results of a test comparing the performance of two such tibial inserts. FIG. 5A shows a first tibial insert 500 having a post 502 extending from a base 504 of the insert 500. The post 502 includes a relief 506 cut out from the anteriomedial side of the post 502, similar to the relief 124 discussed above with respect to post 104. FIG. 5B shows a second tibial insert 550 having a post 552 extending from a base 554. Unlike the insert 500 in FIG. 5A, the insert 550 in FIG. 5B has no medial relief, as the medial wall 556 of the post 552 is a continuous wall with no cut out portion. To demonstrate the effect of the relief 506 in the insert 500, the two model inserts 500 and 550 are coupled with a standard femoral component, for example, femoral component 200 discussed above with respect to FIG. 3A. The femoral component is then articulated against surfaces 508 and 510 of insert 500, or against surfaces 558 and 560 of insert 550. During the articulation, the external rotation of the femoral component relative to the tibial components is measured to demonstrate the effect of the relief 506 in allowing a more natural motion of a new joint.

FIG. 6 shows the results of articulation using the inserts 500 and 550 with a femoral component through a range of about 150 degrees of flexion, starting from full extension (i.e., 0 degrees of flexion) of the knee. The results shown in FIG. 6 illustrate the relative external rotation, measured in degrees, of the femoral component during the test flexion. The line 600 in the graph illustrates the external rotation of a femoral component relative to insert 500 during flexion, while the line 610 illustrates the external rotation of a femoral component relative to insert 550 during rotation. As shown by the two lines 600 and 610, the rotation of the two inserts 500 and 550 is similar during a first segment of the rotation up to a degree D1 of approximately 45 degrees. At degree D1, both the lines 600 at point 602 and the line 610 at point 612 are at about 1.5 degrees of rotation. After the points 602 and 612, the two lines 600 and 610 begin to diverge over a segment 604 of line 600 and a segment 614 of line 610. As shown by segments 604 and 614, the insert 500 with the relief 506 exhibits greater rotation than the insert 550. The rotation of the insert 500 and the insert 550 then reach peaks at or near a degree D2 of flexion at approximately 120 degrees. As shown by point 606 in line 600 and point 616 in line 610, this peak rotation is about 8 degrees for insert 500 and about 6.5 degrees for insert 550. This difference in the peak rotations is a result of the reduced rotational constraint provided by the relief 506 in the insert 500, as illustrated in FIGS. 4A and 4B, and discussed with respect to post 104.

A medial relief thus reduces the rotational constraint of a post but may also reduce the valgus constraint provided by the post. This tradeoff between rotational constraint and valgus constraint may be adequate for a patient whose native anatomy provides sufficient valgus constraint on its own, but may lead to complications if the patient's anatomy does not provide such support. In cases where the anatomy is weak against valgus motion but strong against varus motion, the post relief may be disposed on the posterior-lateral corner of a post, such as post 502, rather than the anteromedial corner. Such a relief would allow the posterior-lateral corner of the post to clear a box wall of a femoral component, allowing for the same rotation shown in FIG. 4B, but may reduce the varus constraint provided by the post. Such an insert would leverage the anatomy's resistance to varus motion and supplement the weak valgus resistant to provide both natural knee motion and adequate support.

Figure 7A:
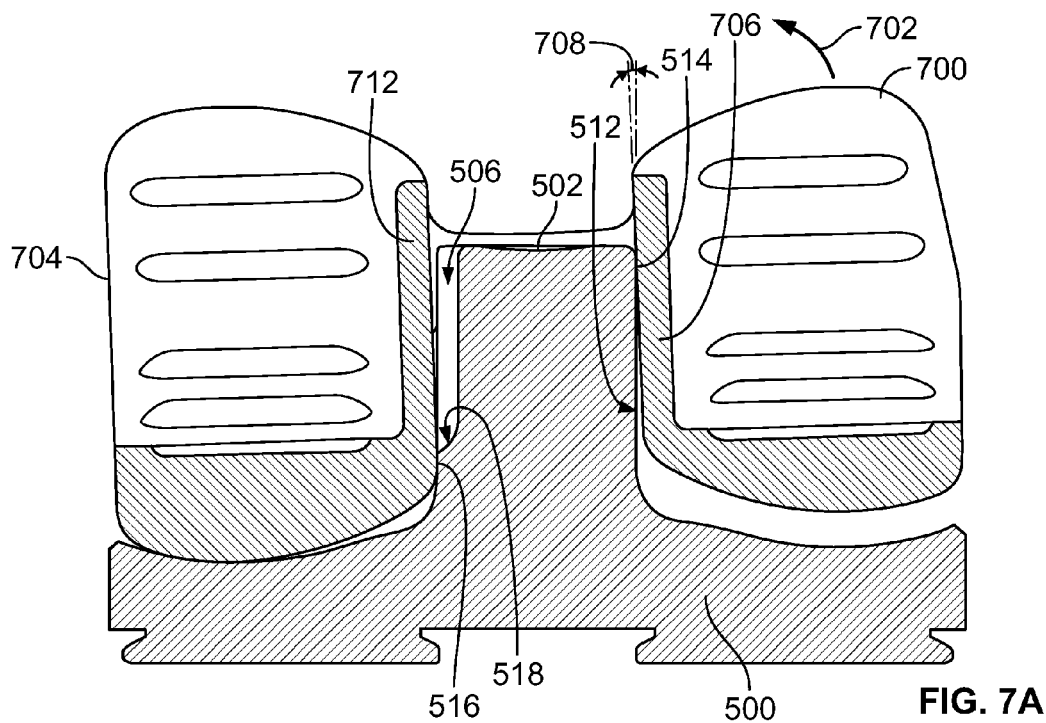
FIG. 7A depicts varus motion of a femoral component coupled with the insert shown in FIG. 5A.

FIGS. 7A-8B illustrate the varus and valgus constraint provided by each of the two inserts 500 and 550. In FIG. 7A, the insert 500 is coupled with a femoral component 700, shown in a cross-sectional view from the anterior side of the femoral component and tibial insert. The femoral component 700 is tilted counter-clockwise in the direction of arrow 702 toward the medial side 704 of the femoral component. This tilting toward the medial side constitutes a varus rotation of the femoral component 700 relative to the insert 500.

The lateral box wall 706 of the femoral component 700 interacts with the post 502 to provide constraint that resists the rotation of the femoral component 700 in the direction of arrow 702. As shown, the box wall 706 contacts the lateral side 512 of the post 502 at a superior corner 514. Because the relief 506 is disposed on the medial side 516 of the post 502, and not on the lateral side 512, the lateral side 512 provides constraint against the varus rotation similar to that provided by standard posterior stabilizing post. In particular, the constraint of the post 502 limits the varus rotation to a degree 708 shown between the lateral side 512 and the box wall 706.

Figure 7B:
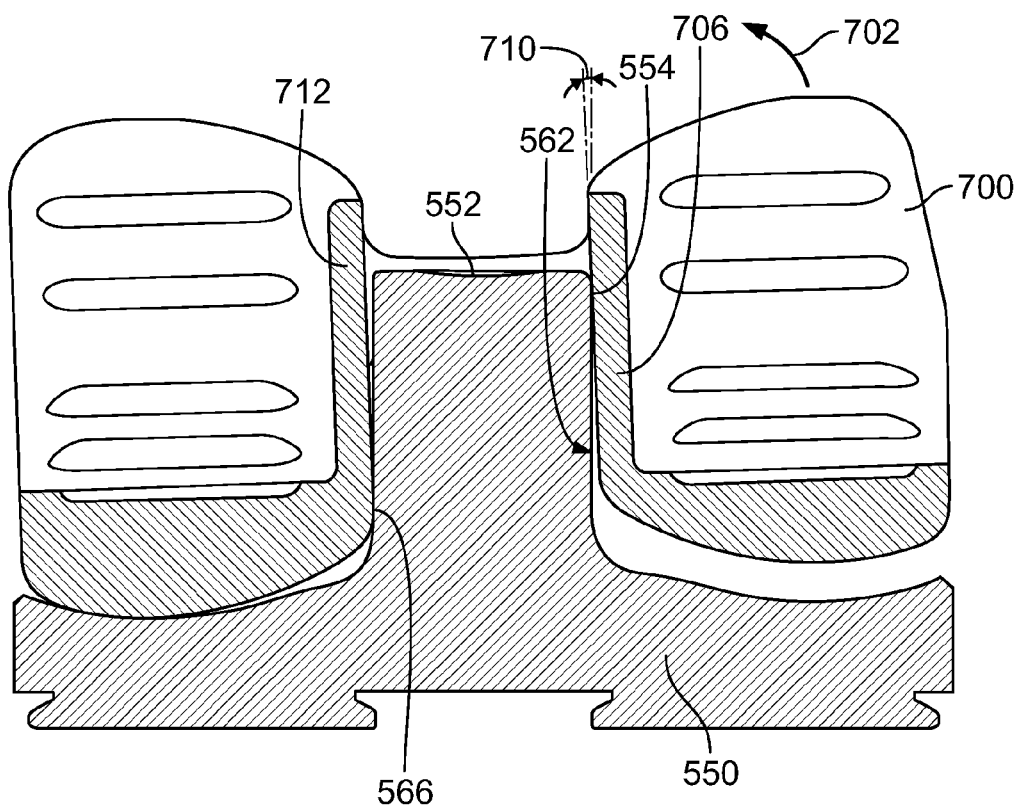
FIG. 7B depicts varus motion of a femoral component coupled with the insert shown in FIG. 5B.

As a comparison to the varus constraint provided by insert 500, FIG. 7B shows varus tilting of the femoral component 700 when coupled with the insert 550. When femoral component 700 is rotated again in the direction of arrow 702, the box wall 706 of the femoral component contacts the lateral wall 562 of the post 552. In particular, the box wall 706 contacts the lateral side 562 at a superior corner 554, similar to the contact at superior corner 514 in FIG. 7A. Because the lateral side 562 and the lateral side 512 have no relief cut-outs, they provide substantially the same constraint against the varus motion of the femoral component 700, and the femoral component 700 rotates only to an angle 710, which is substantially similar to the angle 708, shown in FIG. 7A.

On the medial side of the insert 500, the femoral component 700 contacts the medial side of the post 502 at an inferior portion 516 of the medial side of the post, as shown in FIG. 7A. Likewise, the femoral component 700 contacts the post 552 of insert 550 at an inferior portion 566 of the medial side of the post, as shown in FIG. 7B. Because the inferior portion 516 of the post 502 is located below an inferior shelf 518 of the relief 506, the relief 506 does not compromise the varus constraint provided by the insert 500, and the constraint of the inserts 500 and 550 against varus motion is substantially similar.

Figure 8A:
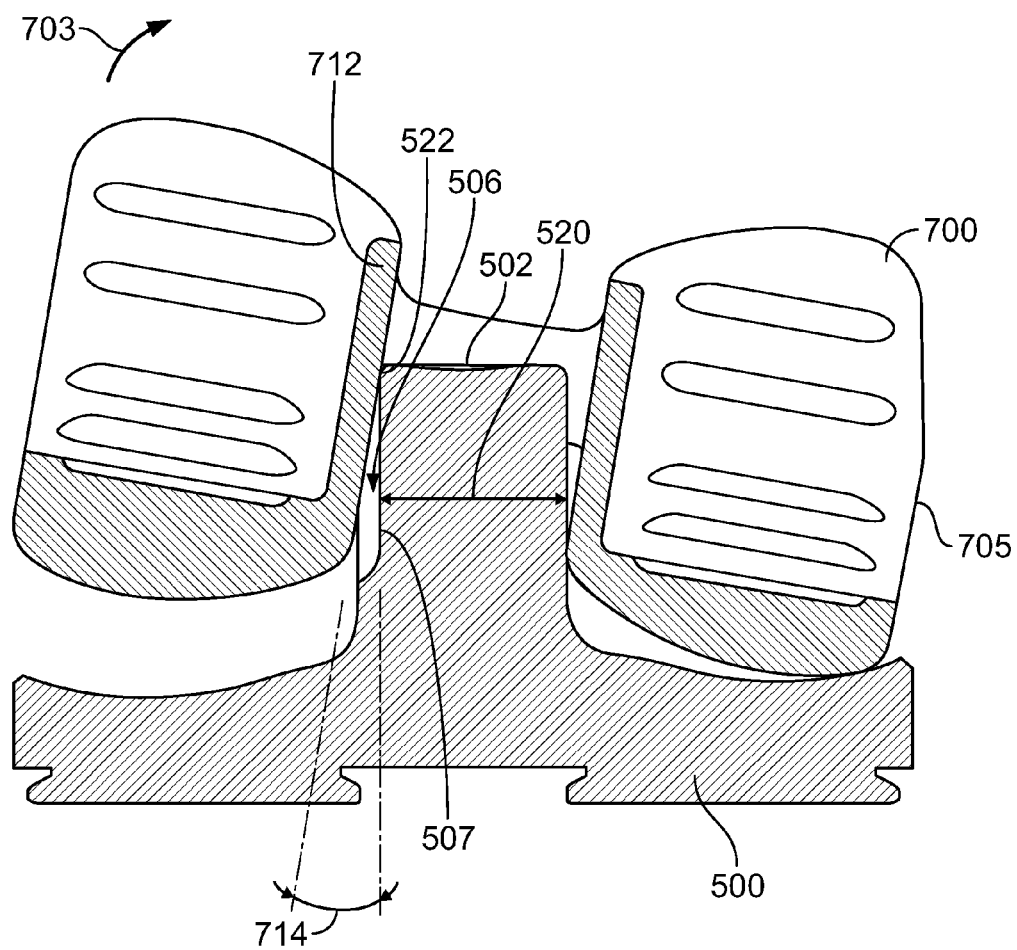
FIG. 8A depicts valgus motion of a femoral component coupled with the insert shown in FIG. 5A.
Figure 8B:
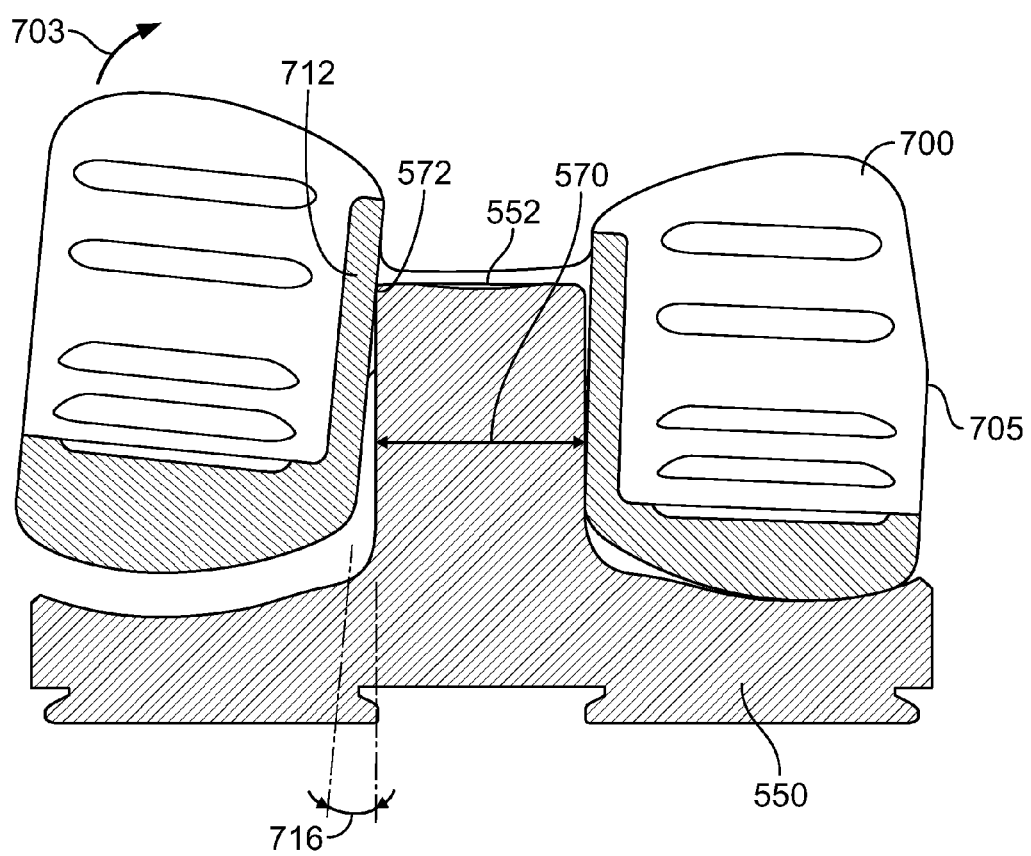
FIG. 8B depicts valgus motion of a femoral component coupled with the insert shown in FIG. 5B.

During a valgus rotation of a femoral component 700 relative to the two inserts 500 and 550, the relief 506 causes differing constraint between the two inserts, as shown in FIGS. 8A and 8B. In FIG. 8A, the femoral component 700 is coupled with the insert 500 and rotated clockwise in the direction of arrow 703, tilting toward the lateral side 705 of the femoral component. When the femoral component 700 tilts in this manner, the medial box wall 712 of the femoral component 700 contacts a superior corner 522 on the medial side of the post 502. The superior corner 522 is on the medial wall 507 of the relief 506, and the contact between the box wall 712 and the superior corner 522 limits the valgus motion of the femoral component 700 in the insert 500 to the angle 714.

In contrast to the insert 500, the insert 550, shown in FIG. 8B, does not have a medial relief, and the post 552 of the insert 550 has a width 570 that is wider than the width 520 of the insert 500. When the femoral component 700 is coupled with the insert 550 and tilted in the direction of arrow 703 toward the lateral side 705 of the femoral component, the medial wall 712 contacts a superior corner 572 of the post 552. This contact limits the valgus motion of the femoral component and insert to an angle 716. Because the post 552 does not have a relief and has a wider width 570, the contact between the wall 712 and the superior corner 572 in FIG. 8B provides a greater constraint to the valgus motion than that provided by the contact between the box wall 712 and the superior corner 522 in FIG. 8A. As a result, the angle 716 is smaller than the angle 714 over which the femoral component 700 may rotate in the valgus direction when coupled with insert 500.

Variations and modifications will occur to those of skill in the art after reviewing this disclosure. The disclosed features may be implemented, in any combination and sub combinations (including multiple dependent combinations and sub-combinations), with one or more other features described herein. The various features described or illustrated above, including any components thereof, may be combined or integrated in other systems. Moreover, certain features may be omitted or not implemented. Examples of changes, substitutions, and alterations are ascertainable by one skilled in the art and could be made without departing from the scope of the information disclosed herein. All references cited herein are incorporated by reference in their entirety and made part of this application.

What is claimed is:

1. A tibial insert, comprising
   a base;
   a post having a vertical axis, a medial and a lateral sidewall, a posterior and an anterior face, a superior end, and an inferior end, the post extending from a superior surface of the base;
   a first junction between the anterior face and medial sidewall, a second junction between the anterior face and the lateral sidewall; and
   a recess in the medial sidewall that extends across the first junction.

2. The tibial insert of claim 1, wherein the recess has a first boundary disposed along the medial sidewall substantially parallel to the vertical axis and a second boundary disposed along the medial sidewall substantially perpendicular to the vertical axis.

3. The tibial insert of claim 2, wherein the second boundary extends across the first junction.

4. The tibial insert of claim 2, wherein the posterior face has a first width between medial and lateral sidewalls, and the anterior face has a second width between the second boundary and lateral sidewall.

5. The tibial insert of claim 4, wherein the first width is greater than the second width.

6. The tibial insert of claim 4, comprising a shelf disposed along the medial sidewall, extending substantially perpendicular to the first boundary.

7. The tibial insert of claim 6, wherein the shelf is disposed superior to the base.

8. The tibial insert of claim 7, wherein the recess has a first depth measured from the first boundary, wherein the first depth has a value of about 0.25 mm to about 1.5 mm.

9. The tibial insert of claim 8, wherein the first depth is about 0.5 mm.

10. The tibial insert of claim 8, wherein the recess has a minimum depth and a maximum depth.

11. A knee prosthesis system, comprising
    a femoral component having first and second condylar surfaces;
    a tibial tray;
    a tibial insert according to claim 1; and
    the tibial insert having first and second bearing surfaces that mate with the respective first and second condylar surfaces.

12. The knee prosthesis system of claim 11, wherein the femoral component includes a box receptacle that receives the post, the receptacle having a first set of opposing walls and a second set of opposing walls, a first wall of the first set of opposing walls being in contact with the medial sidewall at a position inferior to the first boundary and being spaced away from the medial sidewall at a position superior to the first boundary.

13. The knee prosthesis system of claim 12, wherein rotating the post angularly about the vertical axis moves a portion of the anterior face into alignment with the first wall.

14. The knee prosthesis system claim 12, wherein rotating the post angularly about the vertical axis disconnects a portion of the medial sidewall from the first wall.

15. The knee prosthesis system of claim 12, wherein rotating the post angularly about the vertical axis moves the recess toward the medial sidewall.

\* \* \* \* \*